(12) United States Patent
Jin

(10) Patent No.: US 11,191,793 B2
(45) Date of Patent: Dec. 7, 2021

(54) GANODERMA LUCIDUM POLYSACCHARIDES COMPOSITE COMPOSITION

(71) Applicant: GeneFerm Biotechnology Co., Ltd., Tainan (TW)

(72) Inventor: Jinn-Der Jin, Tainan (TW)

(73) Assignee: GENEFERM BIOTECHNOLOGY CO., LTD., Tainan (TW)

( * ) Notice: Subject to any disclaimer, the term of this patent is extended or adjusted under 35 U.S.C. 154(b) by 409 days.

(21) Appl. No.: 16/158,652

(22) Filed: Oct. 12, 2018

(65) Prior Publication Data

US 2020/0023024 A1   Jan. 23, 2020

(30) Foreign Application Priority Data

Jul. 20, 2018 (TW) .................................. 107125245

(51) Int. Cl.
| | |
|---|---|
| *A61K 36/074* | (2006.01) |
| *A61K 31/716* | (2006.01) |
| *A61K 47/12* | (2006.01) |
| *A61P 37/02* | (2006.01) |
| *A61K 47/22* | (2006.01) |

(52) U.S. Cl.
CPC .......... *A61K 36/074* (2013.01); *A61K 31/716* (2013.01); *A61K 47/12* (2013.01); *A61K 47/22* (2013.01); *A61P 37/02* (2018.01); *A61K 2236/11* (2013.01); *A61K 2236/51* (2013.01)

(58) Field of Classification Search
None
See application file for complete search history.

(56) References Cited

U.S. PATENT DOCUMENTS

| | | | | |
|---|---|---|---|---|
| 5,997,875 | A * | 12/1999 | Zhou ...................... | A61K 36/07 424/195.15 |
| 6,464,982 | B1 * | 10/2002 | Lam ....................... | A61K 36/07 424/184.1 |
| 7,135,183 | B1 * | 11/2006 | Wang ................... | A61K 36/074 424/195.15 |

FOREIGN PATENT DOCUMENTS

| | | |
|---|---|---|
| TW | 200607863 A | 3/2006 |
| TW | 200735881 A | 10/2007 |

OTHER PUBLICATIONS

Li et al. (2018) International J. Food Science and Tech. 53: 1942-1953. (Year: 2018).*
He et al. (2017) Int. J. Biol. Macromolec. 97: 228-237. (Year: 2017).*
Kim et al. (2012) J. Agric. Food Chem. 60: 5590-5596. (Year: 2012).*
Li (2000) Pharmaceutical Biology, vol. 38, pp. 33-40. (Year: 2000).*
Nguyen et al. (2012) Carbohydrate Polymers 89: 1117-1122. (Year: 2012).*
Wang et al. (1996) Int. J. Biochem. Cell Biol. vol. 28, No. 5, pp. 601-607. (Year: 1996).*
Wu et al. (2019) Int. J. Biol. Macromolec. 121: 1005-1010. (Year: 2019).*
Yiu et al. (2007) Asia Pac. J. Clin. Nutr. 16(Suppl. 1): 258-260. (Year: 2007).*
Examination Report for TW107125245, dated May 28, 2019, Total of 6 pages.
Search Report for TW107125245, dated May 28, 2019, Total of 1 page.
English Abstract for TW200607863, Total of 1 page.
English Abstract for TW200735881, Total of 1 page.

* cited by examiner

*Primary Examiner* — Russell G Fiebig
(74) *Attorney, Agent, or Firm* — Tracy M Heims; Apex Juris, pllc.

(57) ABSTRACT

A *Ganoderma lucidum* polysaccharides composite composition comprising, based on a total composition: 1 to 5 wt. % β-glucan extract, 1 to 5 wt. % *Ganoderma lucidum* mycelium extract, 1 to 5 wt. % *Trametes versicolor* mycelium extract, 1 to 5 wt. % *Tremella fuciformis* Berk extract, 1 to 5 wt. % *Auricularia auricula-judae* extract, 1 to 5 wt. % *Hericium erinaceus* extract, 1 to 3 wt. % *Ganoderma lucidum* fruiting body extract, and water.

7 Claims, 8 Drawing Sheets

GANODERMA LUCIDUM POLYSACCHARIDES COMPOSITE COMPOSITION

BACKGROUND OF THE INVENTION

Technical Field

The present invention is related to a polysaccharides composition, and more particularly to a *Ganoderma lucidum* polysaccharides composite composition.

Description of Related Art

Polysaccharides produced by fungi could promote immunity. For example, *Ganoderma lucidum* is commonly used as raw materials for producing health food products. β-Glucans are naturally occurring polysaccharides and correlate closely with immunomodulatory effects of polysaccharides.

Conventional polysaccharides health food products could be single-ingredient products and multi-ingredient products, and the multi-ingredient products would have better immunomodulatory effects. With increasing demand for health food products, it is required to develop polysaccharides products having multiple ingredients and good flavor.

BRIEF SUMMARY OF THE INVENTION

In view of the above, an object of the present invention is to provide a *Ganoderma lucidum* polysaccharides composite composition which could promote immunity.

To achieve the object mentioned above, the present invention provides a *Ganoderma lucidum* polysaccharides composite composition comprising, based on a total composition, 1 to 5 wt. % β-glucan extract, 1 to 5 wt. % *Ganoderma lucidum* mycelium extract, 1 to 5 wt. % *Trametes versicolor* mycelium extract, 1 to 5 wt. % *Tremella fuciformis* Berk extract, 1 to 5 wt. % *Auricularia auricula-judae* extract, 1 to 5 wt. % *Hericium erinaceus* extract, 1 to 3 wt. % *Ganoderma lucidum* fruiting body extract, and water.

To achieve the object mentioned above, the present invention provides a method for producing a *Ganoderma lucidum* polysaccharides composite composition, comprising steps of: respectively mixing a fermented culture of *Aureobasidium pullulans*, a fermented culture of *Ganoderma lucidum*, a fermented culture of *Trametes versicolor*, a powdered fruiting body of *Tremella fuciformis* Berk, a powdered fruiting body of *Auricularia auricula-judae*, a powdered fruiting body of *Hericium erinaceus*, and a powdered fruiting body of *Ganoderma lucidum* with water in a ratio by weight of 10:1 to 40:1 for producing a mixture; stirring each of the mixtures at 70 to 100° C. for 2 to 6 hours; filtering each of the mixtures to remove solids; concentrating and heating each of the mixtures for sterilization for producing a β-glucan extract, a *Ganoderma lucidum* mycelium extract, a *Trametes versicolor* mycelium extract, a *Tremella fuciformis* Berk extract, a *Auricularia auricula-judae* extract, a *Hericium erinaceus* extract, and a *Ganoderma lucidum* fruiting body extract; and mixing the extracts together for producing the *Ganoderma lucidum* polysaccharides composite composition.

The advantage of the present invention is that the multi-ingredient *Ganoderma lucidum* polysaccharides composite composition could promote the potential immunomodulatory effects on the specific and non-specific immunity.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

Figure 1:
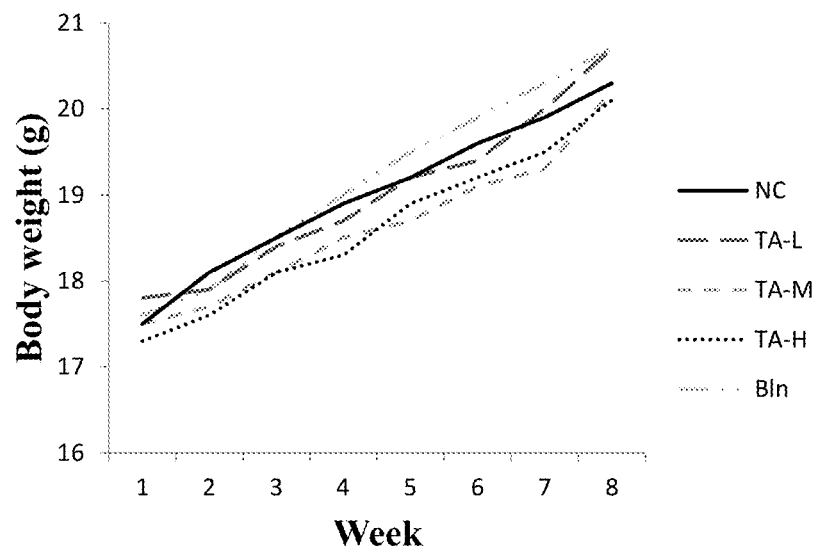
FIG. 1 shows the body weight changes during the evaluation study on the specific immunomodulatory effects.

The following illustrative embodiments and drawings are provided to illustrate the disclosure of the present invention, these and other advantages and effects can be clearly understood by persons skilled in the art after reading the disclosure of this specification.

A *Ganoderma lucidum* polysaccharides composite composition comprises a plurality of fungal extracts and water, wherein the plurality of fungal extracts includes a β-glucan extract, a *Ganoderma lucidum* mycelium extract, a *Trametes versicolor* mycelium extract, a *Tremella fuciformis* Berk extract, an *Auricularia auricula-judae* extract, a *Hericium erinaceus* extract, and a *Ganoderma lucidum* fruiting body extract.

A method for producing the *Ganoderma lucidum* polysaccharides composite composition comprises the following steps.

(1) Polysaccharides Extracted from Fermented Cultures

1.1 Producing Fermented Culture

A microorganism is cultured in a culture medium, wherein the culture medium has a pH of 5.0-6.5 and comprises, based on a total culture medium, 0.5-5.0 wt. % carbon source (e.g., glucose or sucrose), 0.1-1.5 wt. % nitrogen source (e.g., yeast extract, yeast peptones, or soy peptones) and nutrient source (e.g., trace elements and inorganic nutrients). The culture medium is then incubated in air at 20-30° C. for 2-7 days with stirring for producing a fermented culture.

1.2 Producing Polysaccharides Extract

The fermented culture is mixed with water in a ratio by weight of 10:1 to 40:1. The mixture is stirred at 70-100° C. for 2-6 hours, and then filtered to remove solids. The filtered mixture is concentrated and then heated for sterilization to produce a polysaccharides extract.

(2) Polysaccharides Extracted from Fruiting Bodies

2.1 Producing Fruiting Body Mixture

A powdered fruiting body is mixed with water in a ratio by weight of 10:1 to 40:1. The mixture is stirred at 70-100° C. for 2-6 hours. 2.2 Producing polysaccharides extract The mixture is then filtered to remove solids. The filtered mixture is concentrated and then heated for sterilization to produce a polysaccharides extract.

(3) Analysis of Polysaccharides

3.1 β-Glucan Content

The β-glucan extract is mixed with a buffer solution. The mixture is treated with α-amylase, protease, and amyloglucosidase in sequence, and then precipitated with four times volume of ethanol. β-glucan is precipitated from the solution. The precipitation is collected, washed with ethanol, and then dried. The dried precipitation is treated with strong acid and hydrolyzed at high temperature. The β-glucan content is calculated by analyzing the glucose after acid-base neutralization reaction.

3.2 Polysaccharides Concentration

The *Ganoderma lucidum* mycelium extract, the *Trametes versicolor* mycelium extract, the *Tremella fuciformis* Berk extract, the *Auricularia auricula-judae* extract, the *Hericium erinaceus* extract, and the *Ganoderma lucidum* fruiting body extract are respectively diluted to an appropriate concentration and injected into a dialysis membrane (MW: 6000-8000) at a rate of 0.2 L/min for 48 hours. The dialyzed solution is analyzed for polysaccharides concentration by using phenol-sulfuric acid assay. When the carbohydrate is treated with strong acid, the hydroxyl group of the carbohydrate would be combined with the phenol and give an orange color. Whereby, the colorimetric method could be utilized to determine the polysaccharides concentration.

(4) Example

The microorganism of *Aureobasidium pullulans* (BCRC number: 930184), the microorganism of *Ganoderma lucidum*, the microorganism of *Trametes versicolor*, the fruiting body of *Tremella fuciformis* Berk, the fruiting body of *Auricularia auricula-judae*, the fruiting body of *Hericium erinaceus*, and the fruiting body of *Ganoderma lucidum* are utilized to respectively produce the polysaccharides extracts according to the aforementioned steps, and the polysaccharides extracts are mixed together to produce the *Ganoderma lucidum* polysaccharides composite composition of the present invention. The *Ganoderma lucidum* polysaccharides composite composition comprises the ingredients listed below:

| Ingredient | By weight % | Polysaccharides concentration (g/L) |
| --- | --- | --- |
| β-glucan extract | 3.0 | 10 |
| *Ganoderma lucidum* mycelium extract | 3.0 | 5 |
| *Trametes versicolor* mycelium extract | 2.5 | 5 |
| *Tremella fuciformis* Berk extract | 3.0 | 10 |
| *Auricularia auricula-judae* extract | 2.5 | 10 |
| *Hericium erinaceus* extract | 0.5 | 5 |
| *Ganoderma lucidum* fruiting body extract | 0.2 | 5 |
| citric acid | 0.13 | — |
| acesulfame potassium | 0.035 | — |
| orange juice concentrate | 3.4 | — |
| water | 81.735 | — |

Referring to the list, the *Ganoderma lucidum* polysaccharides composite composition of the present invention further comprises a flavor modulator such as citric acid for example, a sweetener such as acesulfame potassium (Ace-K) for example, and a juice concentrate such as orange juice concentrate for example.

The *Ganoderma lucidum* polysaccharides composite composition of the present invention comprises, based on a total composition, 3 wt. % β-glucan extract, 3 wt. % *Ganoderma lucidum* mycelium extract, 2.5 wt. % *Trametes versicolor* mycelium extract, 3 wt. % *Tremella fuciformis* Berk extract, 2.5 wt. % *Auricularia auricula-judae* extract, 0.5 wt. % *Hericium erinaceus* extract, 0.2 wt. % *Ganoderma lucidum* fruiting body extract, 0.13 wt. % citric acid, 0.035 wt. % acesulfame potassium, 3.4 wt. % orange juice concentrate, and 81.735 wt. % water.

Animal experiments are performed to assess the specific and non-specific immunomodulatory effects and the effect of the *Ganoderma lucidum* polysaccharides composite composition. The term "test article" may be used hereinafter to refer to the *Ganoderma lucidum* polysaccharides composite composition.

(1) Specific Immunomodulatory Effects

1.1 Group Designation and Administration Dose for Mice

Female BALB/c mice at 7 weeks old were selected for the animal experiments. As shown in TABLE 1, the mice were divided into 5 groups including negative control group, low dose group, middle dose group, high dose group, and normal control group. Each group had 10 mice. Negative control group mice and normal control group mice were administered sterile water; low dose group mice were administered one fold the recommended human dose of test article; middle dose group mice were administered two fold the recommended human dose of test article, and high dose group mice were administered four fold the recommended human dose of test article. The recommended human dose of the test article was 180 mL/day, and the dose conversion from human to mouse was calculated based on the guidance of the US Food and Drug Administration in 2005, wherein the conversion factor for mouse is 12.3. After freeze-drying, the test article was prepared in sterile water and administered to mice by oral gavage. Mice were administered the test article and negative control article (that is, sterile water) daily via oral gavage for 8 weeks. The administration volume was 10 mL/kg.

TABLE 1

Group designation and administration dose for mouse

| Group | Testing sample | Human dose (Fold) | Administration dose for mouse (mL/kg bw/day) | Lyophilized dosage (g/kg bw/day) | No. of mice | OVA |
|---|---|---|---|---|---|---|
| Negative control (NC) | Sterile water | — | — | — | 10 | + |
| Low dose (TA-L) | Ganoderma lucidum polysaccharides composite composition | 180 mL/day (1X) | 36.9 | 0.9 | 10 | + |
| Middle dose (TA-M) | Ganoderma lucidum polysaccharides composite composition | 360 mL/day (2X) | 73.8 | 1.8 | 10 | + |
| High dose (TA-H) | Ganoderma lucidum polysaccharides composite composition | 720 mL/day (4X) | 147.6 | 3.7 | 10 | + |
| Normal control (Bln) | Sterile water | — | — | — | 10 | — |

"OVA+" mice were immunized with ovalbumin
"OVA—" mice were not immunized with ovalbumin
Dose of human/$60_{(60\ kg\ adult)}$ × $12.3_{(conversion\ factor\ for\ mouse)}$ = Dose of mouse$_{(kg\ b.w./day)}$.

1.2 Immunization

Mice were immunized with ovalbumin (OVA) at Week 4 after administration of the test article. Mice were injected intraperitoneally with 100 μL (25 μg) emulsified in the complete Freund's adjuvant (CFA, Sigma-Aldrich, Cat. no. F5881). Two weeks after the first immunization, mice were given a second intraperitoneal injection of 100 μL OVA (25 μg) emulsified with the incomplete Freund's adjuvant (IFA, Sigma-Aldrich, Cat. no. F5506) at a ratio of 1:1 in order to enhance the OVA-specific immune responses. Mice were sacrificed at the end of study, and whole blood samples and spleens were collected and analyzed for immune cell proliferation, cytokines levels, cell surface markers, and serum immunoglobulins.

1.3 Clinical Observations

During the study period, no clinical signs of illness were observed, including weight loss, hunched back, bleeding lesions, nasal/ocular discharge, hair loss, etc. The mean of body weight at the beginning of the study was 17.3-17.8 g, and the average weight of each group at the end of study was 20.1-20.7 g. The growth rate of experimental animals from each group was about the same. The mean body weight and spleen-to-body weight ratio were not statistically significant among the OVA-sensitized groups including NC, TA-L, TA-M, and TA-H, as shown in TABLE 2 and FIG. 1.

TABLE 2

Body weight changes and spleen-to-body weight ratios

| Week | NC | TA-L | TA-M | TA-H | Bln |
|---|---|---|---|---|---|
| | Body weight (g) | | | | |
| Week 1 | 17.5 ± 0.6 | 17.8 ± 0.8 | 17.5 ± 0.9 | 17.3 ± 0.8 | 17.6 ± 0.8 |
| Week 2 | 18.1 ± 0.4 | 17.9 ± 0.5 | 17.7 ± 0.8 | 17.6 ± 0.7 | 17.9 ± 0.7 |
| Week 3 | 18.5 ± 0.5 | 18.4 ± 0.7 | 18.1 ± 0.5 | 18.1 ± 0.7 | 18.5 ± 0.6 |
| Week 4 | 18.9 ± 0.7 | 18.7 ± 0.9 | 18.5 ± 0.6 | 18.3 ± 0.8 | 19.0 ± 0.6 |
| Week 5 | 19.2 ± 0.7 | 19.2 ± 0.7 | 18.7 ± 0.4 | 18.9 ± 0.8 | 19.5 ± 0.7 |
| Week 6 | 19.6 ± 0.4 | 19.4 ± 0.7 | 19.1 ± 0.5 | 19.2 ± 0.9 | 19.9 ± 0.5 |
| Week 7 | 19.9 ± 0.4 | 20.0 ± 0.8 | 19.3 ± 0.4 | 19.5 ± 0.9 | 20.3 ± 0.5 |
| Week 8 | 20.3 ± 0.3 | 20.7 ± 0.9 | 20.2 ± 0.5 | 20.1 ± 0.8 | 20.7 ± 0.7 |
| | Spleen-to-body weight ratio (%) | | | | |
| | 0.888 ± 0.191 | 0.839 ± 0.152 | 0.868 ± 0.119 | 0.887 ± 0.205 | 0.410 ± 0.028 |

Data were expressed as mean ± standard deviation (S.D.) of 10 mice, and analyzed using one-way ANOVA followed by Duncan's multiple range test.
Spleen-to-body weight ratio = [spleen weight (g)/body weight (g)] × 100.
NC = negative control; TA-L = test article low dose; TA-M = test article middle dose; TA-H = test article high dose; Bln(blank control) = normal control, without OVA immunization.

1.4 Proliferative Responses of Splenocytes

Splenocytes isolated from the spleens were seeded in a 96-well plate at density of $1.0 \times 10^5$ cells/well and treated with OVA for 72 hours. Cell proliferation was measured by $OD_{490nm}$ using the CellTiter 96® AQueous One Solution Cell Proliferation Assay (Promega, Cat. no. G3580). Results were expressed as stimulation index (S.I.), and the formula for calculating S.I. is shown below:

$$\text{Stimulation index } (S.I.) = \frac{OD_{490\,nm} \text{ of OVA-stimulated cells}}{OD_{490\,nm} \text{ of unstimulated cells}}$$

Figure 2:
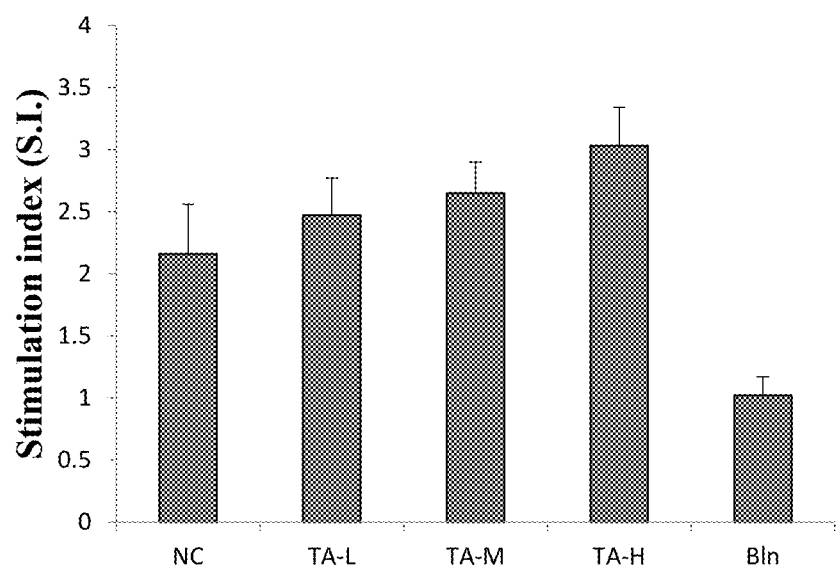
FIG. 2 shows the proliferative responses of mouse splenocytes according to the evaluation study on the specific immunomodulatory effects.

As shown in TABLE 3 and FIG. 2, the proliferative responses to OVA stimulation in the OVA-sensitized groups including NC, TA-L, TA-M, and TA-H were significantly increased as compared to the Bln group ($p<0.05$). Among the OVA-sensitized groups, the proliferative responses induced by OVA were significantly enhanced in the TA-L, TA-M, and TA-H groups in comparison with the NC group ($p<0.05$). The result indicated that the test article promotes the proliferation of splenocytes stimulated by OVA.

TABLE 3

Proliferative responses of mouse splenocytes

| Group | Dose (g/kg/day) | Stimulation index(S.I.) OVA(25 μg/mL) |
|---|---|---|
| NC | — | 2.16 ± 0.40 |
| TA-L | 0.9 | 2.47 ± 0.30 |
| TA-M | 1.8 | 2.65 ± 0.25 |
| TA-H | 3.7 | 3.03 ± 0.31 |
| Bln | — | 1.02 ± 0.15 |

Data were expressed as mean ± standard deviation (S.D.) of 10 mice, and analyzed using one-way ANOVA followed by Duncan's multiple range test.
NC = negative control; TA-L = test article low dose; TA-M = test article middle dose; TA-H = test article high dose; Bln(blank control) = normal control, without OVA immunization.
Stimulation index (S.I.) = $OD_{490\ nm}$ of OVA-stimulated cells/$OD_{490\ nm}$ of unstimulated cells.

1.5 Splenocyte Cytokine Production

Splenocytes (0.5 to $2 \times 10^6$ cells/well) were treated with 25 μg/mL OVA in a 24-well plate. After incubation at 37° C., 5% CO2 for 48 to 72 hours, cell-free supernatants were collected after centrifugation (300 g, 4° C., 10 minutes), and cytokines including Interleukin-2 (IL-2, eBioscience, Cat. no. 88-7024), Interleukin-4 (IL-4, eBioscience, Cat. no. 88-7044), Interleukin-5 (IL-5, eBioscience, Cat. no. 88-7054), Interleukin-10 (IL-10, eBioscience, Cat. no. 88-7104), Interferon γ (IFN-γ, eBioscience, Cat. no. 88-7314) were measured by ELISA assay kit after 72 hours OVA stimulation. In addition, Tumor necrosis factor-α(TNF-α, eBioscience, Cat. no. 88-7324) was measured after 48 hours OVA stimulation.

1.5.1 IL-2

Figure 3:
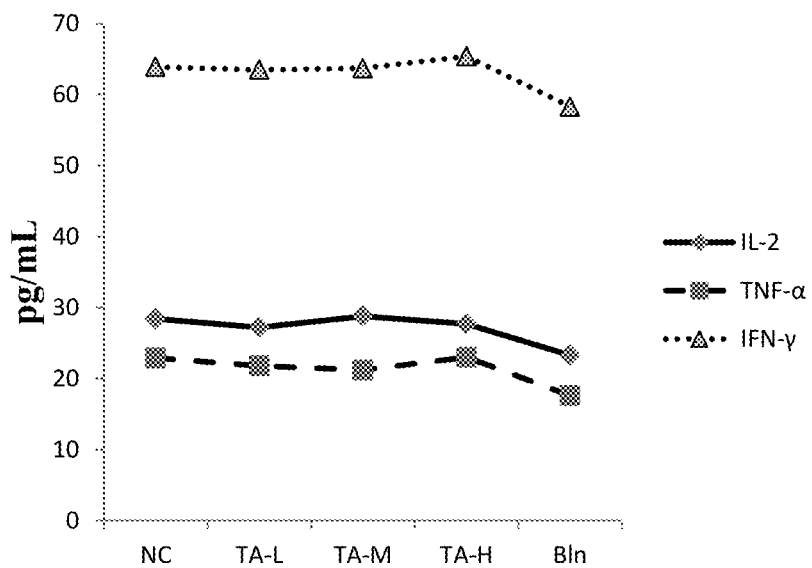
FIG. 3 shows the IL-2, TNF-α, and IFN-γ production without OVA stimulation according to the evaluation study on the specific immunomodulatory effects.
Figure 4:
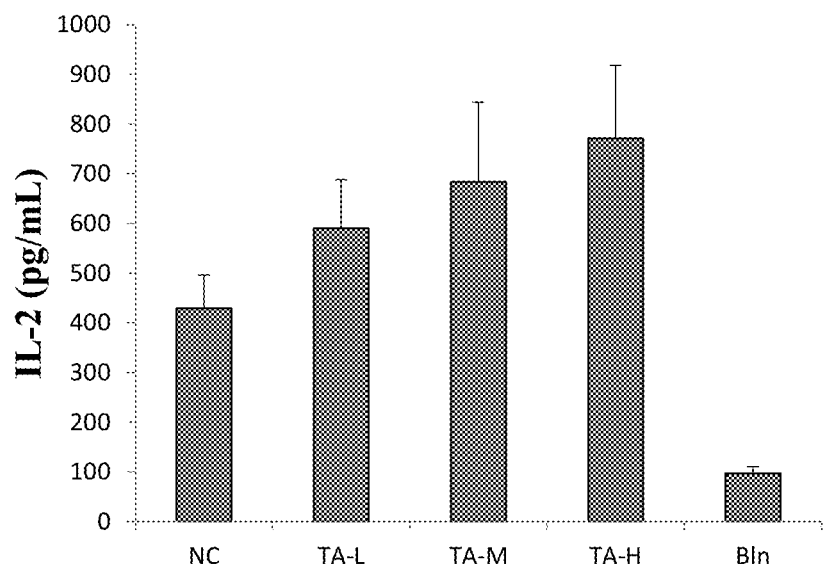
FIG. 4 shows the IL-2 production after OVA stimulation according to the evaluation study on the specific immunomodulatory effects.

As shown in TABLE 4 and FIGS. 3 and 4, there were no significant differences in basal levels (without OVA stimulation) of IL-2 release among all groups ($p>0.05$). The IL-2 level was significantly increased in the OVA-sensitized groups including NC, TA-L, TA-M, and TA-H as compared to the Bln group ($p<0.05$), and thus an OVA-sensitization model used in this study was successfully established. After OVA stimulation, the IL-2 level was significantly increased in the TA-L, TA-M, and TA-H groups as compared to the NC group ($p<0.05$). The result indicated that the test article promotes OVA-induced IL-2 secretion.

TABLE 4

Cytokines production

| Group | Unstimulated basal level | OVA(25 μg/mL) |
|---|---|---|
| IL-2(pg/mL) | | |
| NC | 28.4 ± 4.4 | 429.1 ± 66.7 |
| TA-L | 27.2 ± 5.7 | 590.4 ± 97.8 |
| TA-M | 28.8 ± 5.0 | 683.3 ± 160.8 |
| TA-H | 27.7 ± 4.5 | 771.3 ± 146.4 |
| Bln | 23.3 ± 2.6 | 96.7 ± 13.7 |
| IL-4(pg/mL) | | |
| NC | 31.3 ± 2.4 | 103.1 ± 16.4 |
| TA-L | 31.3 ± 4.7 | 104.7 ± 19.7 |
| TA-M | 32.5 ± 1.8 | 104.4 ± 24.6 |
| TA-H | 33.1 ± 4.7 | 102.4 ± 21.0 |
| Bln | 29.3 ± 1.3 | 59.3 ± 11.9 |
| IL-5(pg/mL) | | |
| NC | 21.8 ± 2.1 | 90.0 ± 8.9 |
| TA-L | 22.7 ± 1.5 | 87.1 ± 14.6 |
| TA-M | 20.6 ± 2.6 | 87.4 ± 8.7 |
| TA-H | 20.9 ± 3.2 | 80.7 ± 11.6 |
| Bln | 19.3 ± 3.4 | 42.5 ± 2.8 |
| IL-10(pg/mL) | | |
| NC | 213.6 ± 19.0 | 1251.1 ± 140.5 |
| TA-L | 202.5 ± 17.2 | 1195.6 ± 195.7 |
| TA-M | 211.6 ± 17.9 | 1178.9 ± 188.1 |
| TA-H | 213.3 ± 15.7 | 1156.7 ± 178.8 |
| Bln | 196.9 ± 5.2 | 355.6 ± 43.8 |
| TNF-α | | |
| NC | 22.9 ± 5.6 | 243.2 ± 29.8 |
| TA-L | 21.8 ± 6.2 | 245.2 ± 25.5 |
| TA-M | 21.2 ± 3.5 | 264.0 ± 32.3 |
| TA-H | 23.0 ± 3.3 | 273.7 ± 36.4 |
| Bln | 17.6 ± 2.6 | 77.3 ± 7.9 |
| IFN-γ | | |
| NC | 63.9 ± 16.6 | 1651.6 ± 349.7 |
| TA-L | 63.5 ± 9.4 | 2477.1 ± 403.7 |
| TA-M | 63.7 ± 12.8 | 2986.9 ± 518.9 |
| TA-H | 65.4 ± 11.8 | 3423.3 ± 517.4 |
| Bln | 58.3 ± 12.2 | 482.7 ± 73.5 |

Data were expressed as mean ± standard deviation (S.D.) of 10 mice, and analyzed using one-way ANOVA followed by Duncan's multiple range test.
NC = negative control; TA-L = test article low dose; TA-M = test article middle dose; TA-H = test article high dose; Bln(blank control) = normal control, without OVA immunization.

1.5.2 IL-4

Further referring to TABLE 4, there were no significant differences in basal levels (without OVA stimulation) of IL-4 release among all groups ($p>0.05$). The IL-4 level was significantly increased in the OVA-sensitized groups including NC, TA-L, TA-M, and TA-H as compared to the Bln group ($p<0.05$), and thus an OVA-sensitization model used in this study was successfully established. After OVA stimulation, there were no significant differences in IL-4 level among the OVA-sensitized groups including NC, TA-L, TA-M, and TA-H ($p>0.05$).

1.5.3 IL-5

Further referring to TABLE 4, there were no significant differences in basal levels (without OVA stimulation) of IL-5 release among all groups ($p>0.05$). The IL-5 level was significantly increased in the OVA-sensitized groups including NC, TA-L, TA-M, and TA-H as compared to the Bln group ($p<0.05$), and thus an OVA-sensitization model used in this study was successfully established. After OVA stimulation, there were no significant differences in IL-5 level among the OVA-sensitized groups including NC, TA-L, TA-M, and TA-H (p>0.05).

1.5.4 IL-10

Further referring to TABLE 4, there were no significant differences in basal levels (without OVA stimulation) of IL-10 release among all groups (p>0.05). The IL-10 level was significantly increased in the OVA-sensitized groups including NC, TA-L, TA-M, and TA-H as compared to the Bln group (p<0.05), and thus an OVA-sensitization model used in this study was successfully established. After OVA stimulation, there were no significant differences in IL-10 level among the OVA-sensitized groups including NC, TA-L, TA-M, and TA-H (p>0.05).

1.5.5 TNF-α

Figure 5:
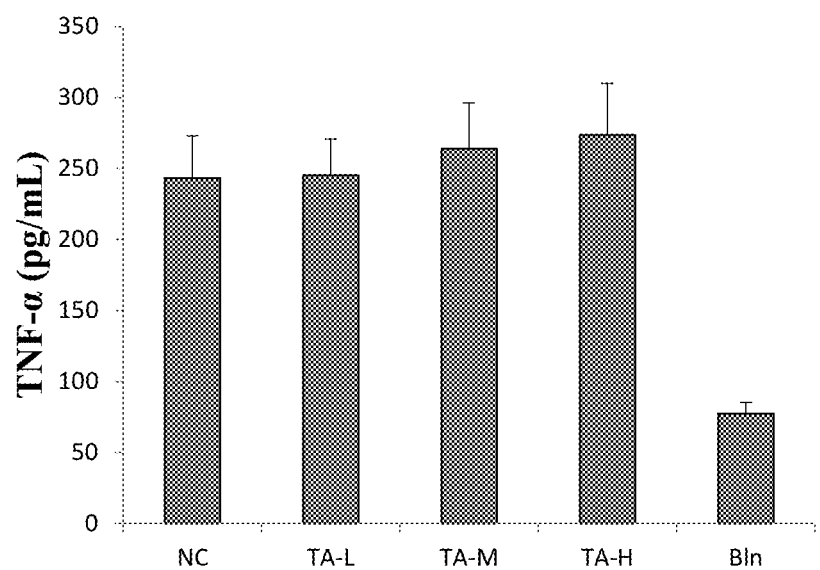
FIG. 5 shows the TNF-α production after OVA stimulation according to the evaluation study on the specific immunomodulatory effects.

Further referring to TABLE 4 and FIGS. 3 and 5, there were no significant differences in basal levels (without OVA stimulation) of TNF-α release among all groups (p>0.05). The TNF-α level was significantly increased in the OVA-sensitized groups including NC, TA-L, TA-M, and TA-H as compared to the Bln group (p<0.05), and thus an OVA-sensitization model used in this study was successfully established. After OVA stimulation, TNF-α level was increased in a dose-dependent manner, and a significant difference was found in the TA-H group as compared to the NC group (p<0.05).

1.5.6 IFN-γ

Figure 6:
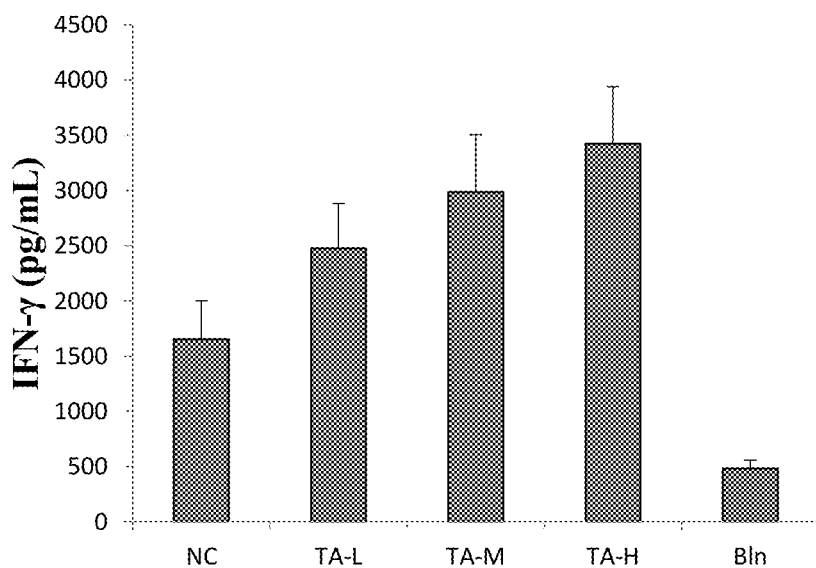
FIG. 6 shows the IFN-γ production after OVA stimulation according to the evaluation study on the specific immunomodulatory effects.

Further referring to TABLE 4 and FIGS. 3 and 6, there were no significant differences in basal levels (without OVA stimulation) of IFN-γ release among all groups (p>0.05). IFN-γ level was significantly increased in the OVA-sensitized groups including NC, TA-L, TA-M, and TA-H as compared to the Bln group (p<0.05), and thus an OVA-sensitization model used in this study was successfully established. After OVA stimulation, the IFN-γ level was significantly increased in the TA-L, TA-M, and TA-H groups as compared to the NC group (p<0.05). The result indicated that the test article promotes OVA-induced IFN-γ secretion.

1.6 Serum Levels of Immunoglobulins

Serum samples were collected after the whole blood sample was centrifugated, and stored at −80° C. for further analysis for anti-OVA IgG2a, anti-OVA IgG1, and anti-OVA IgE antibodies detected by an indirect ELISA. Briefly, 96-well plates were coated with OVA at 4° C. for 24 hours. After washing, serum samples were added to triplicate wells. The plates were incubated at 37° C. for 1 hour, and then washed with phosphate buffered saline with Tween 20 (PBST). After incubation with secondary antibody conjugated with horseradish peroxidase (HRP), substrate 3,3',5,5'-tetramethylbenzidine (TMB) (SureBlue Reserve TMB Microwell Peroxidase Substrate) was added to each well after washing with PBST. Optical density (OD) was detected at 450 nm with ELISA reader. Levels of OVA-specific antibodies were expressed as ELISA unit (EU) and calculated as follows:

ELISA Unit (EU) = $(A_{sample} - A_{blank}) / (A_{positive} - A_{blank})$

Figure 7:
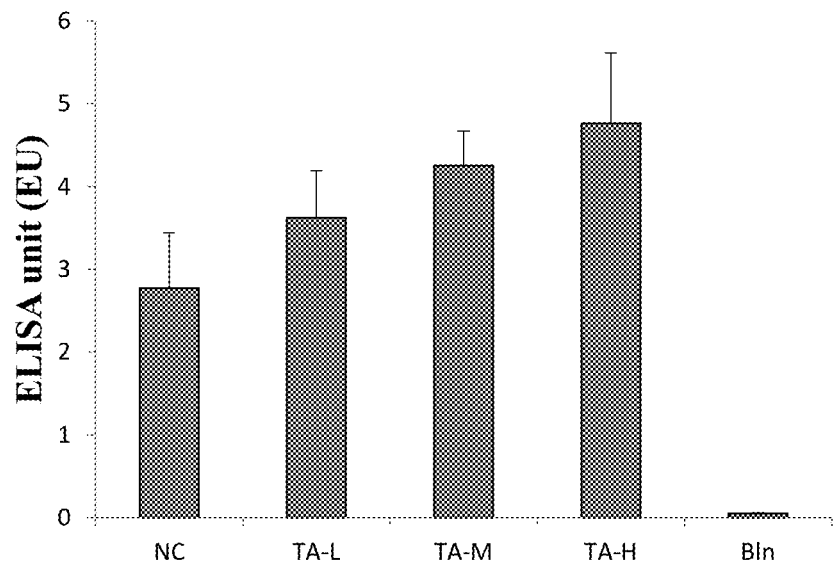
FIG. 7 shows the anti-OVA IgG2a antibodies production according to the evaluation study on the specific immunomodulatory effects.

As shown in TABLE 5 and FIG. 7, serum levels of anti-OVA IgG2a, anti-OVA IgG1, and anti-OVA IgE antibodies in all OVA-sensitized groups including NC, TA-L, TA-M, and TA-H were significantly increased (p<0.05) as compared to the Bln group (without OVA stimulation), and thus an OVA-sensitization model used in this study was successfully established. Anti-OVA IgG2a antibodies were significantly increased in the TA-L, TA-M, and TA-H groups as compared to the NC group (p<0.05). The result indicated that the test article promotes the production of anti-OVA IgG2a antibodies in OVA-sensitized mice.

TABLE 5

OVA-specific antibody levels

| Group | OVA-specific antibody (ELISA unit, EU) | | |
|---|---|---|---|
| | anti-OVA IgG1 | anti-OVA IgG2a | anti-OVA IgE |
| NC | 2.09 ± 0.09 | 2.77 ± 0.67 | 0.07 ± 0.03 |
| TA-L | 2.10 ± 0.08 | 3.62 ± 0.57 | 0.06 ± 0.02 |
| TA-M | 2.08 ± 0.07 | 4.25 ± 0.42 | 0.06 ± 0.01 |
| TA-H | 2.01 ± 0.15 | 4.76 ± 0.85 | 0.05 ± 0.02 |
| Bln | 0.03 ± 0.01 | 0.05 ± 0.01 | 0.03 ± 0.01 |

Data were expressed as mean ± standard deviation (S.D.) of 10 mice, and analyzed using one-way ANOVA followed by Duncan's multiple range test.
NC = negative control; TA-L = test article low dose; TA-M = test article middle dose; TA-H = test article high dose; Bln(blank control) = normal control, without OVA immunization.

1.7 Cell Surface Marker Analysis

Splenocytes ($5 \times 10^5$ cells/well) were stained with fluorescence-conjugated monoclonal antibodies against T4 cells markers (CD4+/CD3+), T8 cells markers (CD8+/CD3+), T cells markers (CD3+/CD45+), B cells markers (CD19+/CD45+), and NK cells markers (PanNK+/CD45+). Different lymphocyte populations by cell surface markers were quantified by flow cytometry. As shown in TABLE 6, there were no significant differences among all groups.

TABLE 6

Cell surface marker analysis
Immune cell type (%)

| Group | T4 cell (CD4+, CD3+) | T8 cell (CD8+, CD3+) | Tcell (CD3+, CD45+) |
|---|---|---|---|
| NC | 23.40 ± 2.14 | 11.30 ± 1.83 | 36.29 ± 3.35 |
| TA-L | 21.83 ± 2.25 | 10.46 ± 2.59 | 35.74 ± 3.68 |
| TA-M | 23.66 ± 3.14 | 11.02 ± 2.69 | 35.67 ± 4.57 |
| TA-H | 23.85 ± 3.03 | 11.53 ± 1.35 | 38.29 ± 4.09 |
| Bln | 25.71 ± 2.94 | 11.56 ± 2.00 | 39.52 ± 2.98 |

Cell surface marker analysis
Immune cell type (%)

| Group | Bcell (CD19+, CD45+) | NK cell (PanNK+, CD45+) |
|---|---|---|
| NC | 53.28 ± 3.22 | 6.94 ± 0.81 |
| TA-L | 53.91 ± 3.27 | 7.15 ± 0.83 |
| TA-M | 53.23 ± 4.35 | 7.00 ± 0.92 |
| TA-H | 52.13 ± 5.44 | 8.14 ± 1.41 |
| Bln | 50.84 ± 3.88 | 7.50 ± 0.86 |

Data were expressed as mean ± standard deviation (S.D.) of 10 mice, and analyzed using one-way ANOVA followed by Duncan's multiple range test.
NC = negative control; TA-L = test article low dose; TA-M = test article middle dose; TA-H = test article high dose; Bln(blank control) = normal control, without OVA immunization.

With the aforementioned results, as shown in TABLE 7, the test article could promote OVA-induced lymphocyte proliferation and the production of anti-OVA IgG2a antibodies. In addition, after OVA stimulation, the test article could promote the production of IL-2, IFN-γ, and TNF-α. Whereby, the *Ganoderma lucidum* polysaccharides composite composition has the potential immunomodulatory effects on specific immunity

TABLE 7

Summary of the immunomodulatory effects of
the *Ganoderma lucidum* polysaccharides composite
composition on the specific immunity

| Testing parameters | | | TA-L | TA-M | TA-H |
|---|---|---|---|---|---|
| Splenocyte proliferation | | OVA stimulation | p < 0.05↑ | p < 0.05↑ | p < 0.05↑ |
| Cytokines production | IL-2 | Yes | p < 0.05↑ | p < 0.05↑ | p < 0.05↑ |
| | IL-4 | Yes | — | — | — |
| | IL-5 | Yes | — | — | — |
| | IL-10 | Yes | — | — | — |
| | TNF-α | Yes | — | — | p < 0.05↑ |
| | IFN-γ | Yes | p < 0.05↑ | p < 0.05↑ | p < 0.05↑ |
| Spleen lymphocyte populations | T4 cell | | — | — | — |
| | T8 cell | | — | — | — |
| | T cell | | — | — | — |
| | B cell | | — | — | — |
| | NK cell | | — | — | — |
| Serum antibody | anti-OVA IgG2a | | p < 0.05↑ | p < 0.05↑ | p < 0.05↑ |
| | anti-OVA IgG1 | | — | — | — |
| | anti-OVA IgE | | — | — | — |

—: no significant difference as compared to the NC group
$p < 0.05↑$: significantly increased as compared to the NC group
$p < 0.05↓$: significantly decreased as compared to the NC group (2) Non-Specific Immunomodulatory Effects 2.1 Group Designation and Administration Dose for Mice Female BALB/c mice at 7 weeks old were selected for the animal experiments. As shown in TABLE 8, the mice were divided into 4 groups including negative control group, low dose group, middle dose group, and high dose group. Each group had 10 mice. Negative control group mice were administered sterile water; low dose group mice were administered one fold the recommended human dose of test article; middle dose group mice were administered two fold the recommended human dose of test article, and high dose group mice were administered four fold the recommended human dose of test article. The recommended human dose of test article was 180 mL/day, and the dose conversion from human to mouse was calculated based on the guidance of the US Food and Drug Administration in 2005, wherein the conversion factor for mouse is 12.3. After freeze-drying, the test article was prepared in sterile water and administered to mice by oral gavage. Mice were administered the test article and negative control article (that is, sterile water) daily via oral gavage for 6 weeks. The administration volume was 10 mL/kg.

TABLE 8

Group designation and administration dose for mouse

| Group | Testing sample | Human dose (Fold) | Administration dose for mouse (mL/kg bw/day) | Lyophilized dosage (g/kg bw/day) | No. of mice |
|---|---|---|---|---|---|
| Negative control (NC) | Sterile water | — | — | — | 10 |
| Low dose (TA-L) | *Ganoderma lucidum* polysaccharides composite composition | 180 mL/day (1X) | 36.9 | 0.9 | 10 |
| Middle dose (TA-M) | *Ganoderma lucidum* polysaccharides composite composition | 360 mL/day (2X) | 73.8 | 1.8 | 10 |
| High dose (TA-H) | *Ganoderma lucidum* polysaccharides composite composition | 720 mL/day (4X) | 147.6 | 3.7 | 10 |

Dose Of human/$60_{(60\ kg\ adult)}$ × $12.3_{(conversion\ factor\ for\ mouse)}$ = Dose of mouse$_{(kg\ b.w./day)}$.

2.2 Test Sample Collections

Mice were sacrificed at the end of study, and whole blood samples, spleens, and macrophages isolated from the abdominal cavity were collected and analyzed for immune cell proliferation, cytokines levels, cell surface markers, natural killer (NK) cell cytolytic activity, serum immunoglobulins, and phagocytic activity.

2.3 Clinical Observations

Figure 8:
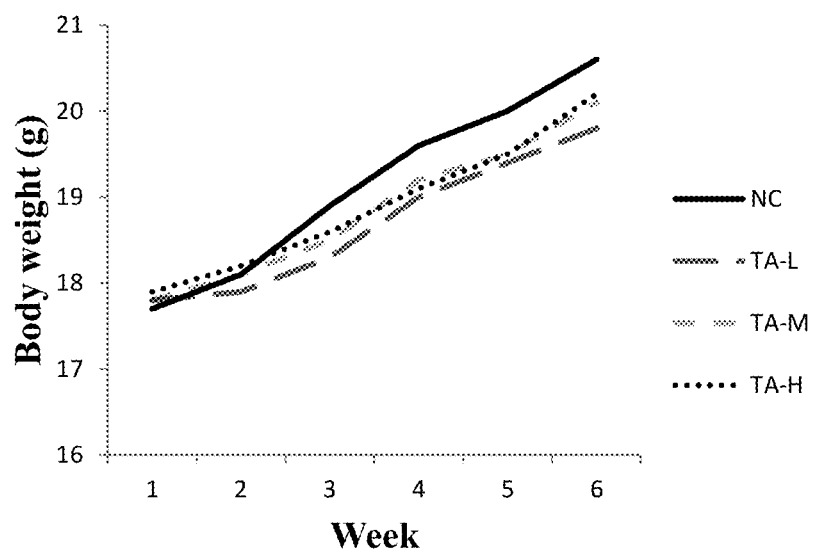
FIG. 8 shows the body weight changes during the evaluation study on the non-specific immunomodulatory effects.

During the study period, no clinical signs of illness were observed, including weight loss, hunched back, bleeding lesions, nasal/ocular discharge, hair loss, etc. The mean of body weight at the beginning of the study was 17.7-17.9 g, and the average weight of each group at the end of study was 19.8-20.6 g. The growth rate of experimental animals from each group was about the same (p>0.05). The mean body weight and spleen-to-body weight ratio were not statistically significant among all study groups, as shown in TABLE 9 and FIG. 8.

TABLE 9

Body weight changes and spleen-to-body weight ratios

| | Group | | | |
|---|---|---|---|---|
| Week | NC | TA-L | TA-M | TA-H |
| | Body weight (g) | | | |
| Week 1 | 17.7 ± 0.5 | 17.8 ± 0.7 | 17.8 ± 0.7 | 17.9 ± 0.8 |
| Week 2 | 18.1 ± 1.1 | 17.9 ± 0.8 | 18.1 ± 0.8 | 18.2 ± 1.1 |
| Week 3 | 18.9 ± 1.1 | 18.3 ± 0.7 | 18.5 ± 0.8 | 18.6 ± 1.1 |
| Week 4 | 19.6 ± 1.1 | 19.0 ± 0.8 | 19.2 ± 1.0 | 19.1 ± 1.2 |
| Week 5 | 20.0 ± 1.0 | 19.4 ± 0.9 | 19.5 ± 1.0 | 19.5 ± 1.2 |
| Week 6 | 20.6 ± 0.9 | 19.8 ± 0.8 | 20.1 ± 1.0 | 20.2 ± 1.4 |
| | Spleen-to-body weight ratio (%) | | | |
| | 0.448 ± 0.051 | 0.444 ± 0.046 | 0.462 ± 0.049 | 0.461 ± 0.040 |

Data were expressed as mean ± standard deviation (S.D.) of 10 mice, and analyzed using one-way ANOVA followed by Duncan's multiple range test.
Spleen-to-body weight ratio = [spleen weight (g)/body weight (g)] × 100.
NC = negative control; TA-L = test article low dose; TA-M = test article middle dose; TA-H = test article high dose.

2.4 Proliferative Responses of Splenocytes

Splenocytes ($2.0×10^5$ cells/well) isolated from the spleens were treated with mitogen Concanavalin A (Con A) and lipopolysaccharide (LPS) for 72 hours to stimulate T cells and B cells proliferation. Cell proliferation was measured by $OD_{490nm}$ using CellTiter 96® AQueous One Solution Cell Proliferation Assay (Promega, Cat. no. G3580). Results were expressed as stimulation index (S.I.), and the formula for calculating S.I. is shown below:

$$\text{Stimulation index } (S.I.) = \frac{OD_{490nm} \text{ of Con A or LPS treated cells}}{OD_{490nm} \text{ of unstimulated cells}}$$

Figure 9:
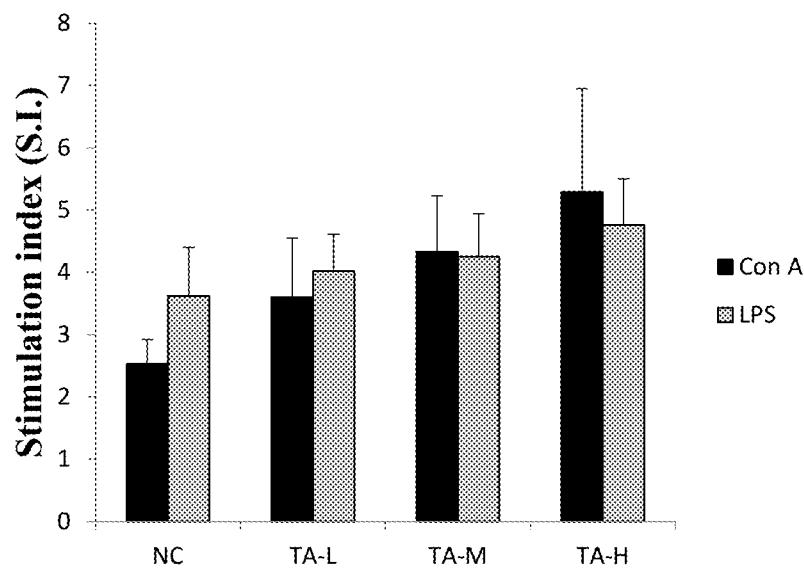
FIG. 9 shows the proliferative responses of mouse splenocytes according to the evaluation study on the non-specific immunomodulatory effects.

As shown in TABLE 10 and FIG. 9, the proliferative responses to Con A stimulation in the TA-L, TA-M, and TA-H groups were significantly increased as compared to the NC group (p<0.05). In addition, only the TA-H group showed a significant increase in cell proliferation after LPS stimulation. The result indicated that the test article promotes the proliferation of splenocytes stimulated by Con A and LPS.

TABLE 10

Proliferative responses of mouse splenocytes

| | | Stimulation index(S.I.) | |
|---|---|---|---|
| Group | Dose (g/kg/day) | Con A (5.0 µg/mL) | LPS (10.0 µg/mL) |
| NC | — | 2.53 ± 0.39 | 3.62 ± 0.78 |
| TA-L | 0.9 | 3.60 ± 0.95 | 4.02 ± 0.59 |
| TA-M | 1.8 | 4.33 ± 0.90 | 4.25 ± 0.69 |
| TA-H | 3.7 | 5.29 ± 1.66 | 4.76 ± 0.74 |

Data were expressed as mean ± standard deviation (S.D.) of 10 mice, and analyzed using one-way ANOVA followed by Duncan's multiple range test.
NC = negative control; TA-L = test article low dose; TA-M = test article middle dose; TA-H = test article high dose.

2.5 NK Cell Cytolytic Activity

YAC-1 cells (mouse lymphoma cells) were used as target cells for mouse NK cells, and pre-labeled with PKH67 dye by using PKH67 Fluorescent Cell Linker Kits (Sigma-Aldrich). Splenocytes were incubated with PKH67-labeled NK-sensitive YAC-1 target cells at a ratio of 10:1 and 25:1 at 37° C. for 4 hours, and then treated with 50 µL Propidium iodine (PI) solution (0.1 mg/mL). NK cell-mediated cytotoxicity against pre-labeled YAC-1 cells was measured by flow cytometry following PI staining.

Figure 10:
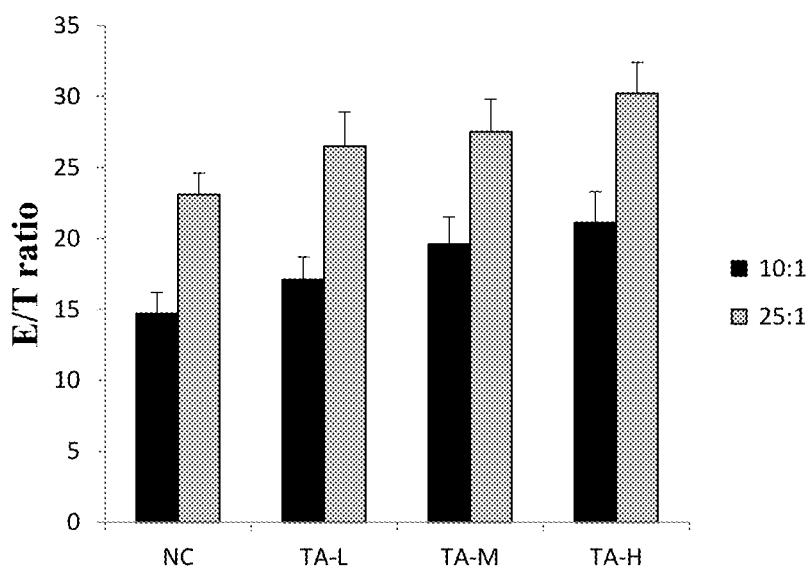
FIG. 10 shows the NK cell cytolytic activity according to the evaluation study on the non-specific immunomodulatory effects.

As shown in TABLE 11 and FIG. 10, NK cell cytolytic activity was significantly induced in the TA-L, TA-M, and TA-H groups as compared to the NC group at the ratio of 10:1 and 25:1 (p<0.05). The result indicated that the splenic NK cell activity was significantly enhanced by the test article.

TABLE 11

NK cell cytolytic activity

| | Dose | E/T ratio | |
|---|---|---|---|
| Group | (g/kg/day) | 10:1 | 25:1 |
| NC | — | 14.7 ± 1.5 | 23.1 ± 1.5 |
| TA-L | 0.9 | 17.1 ± 1.6 | 26.5 ± 2.4 |
| TA-M | 1.8 | 19.6 ± 1.9 | 27.5 ± 2.3 |
| TA-H | 3.7 | 21.1 ± 2.2 | 30.2 ± 2.2 |

Data were expressed as mean ± standard deviation (S.D.) of 10 mice, and analyzed using one-way ANOVA followed by Duncan's multiple range test.
NC = negative control; TA-L = test article low dose; TA-M = test article middle dose; TA-H = test article high dose.
E/T ratio = Effector cell (NKcell)/target cell (YAC-1 cell) ratio 2.6 Phagocytic Activity of Peritoneal Macrophages Macrophages isolated from the abdominal cavity of mice were incubated with fluorescein-labeled opsonized *E. coli* at 37° C. for 2 hours at multiplicity of infection (M.O.I.) of 12.5, 25, and 50. Phagocytosis was assessed by flow cytometry.

Figure 11:
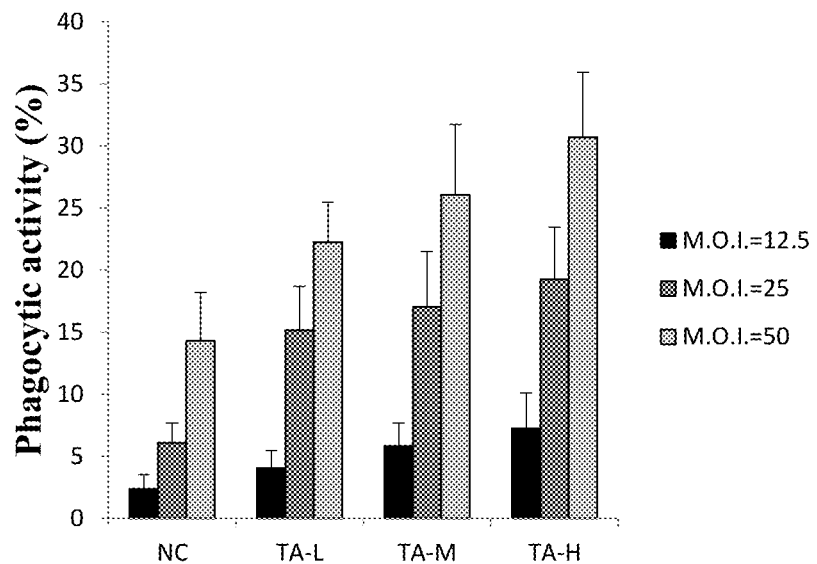
FIG. 11 shows the phagocytic activity of peritoneal macrophages according to the evaluation study on the non-specific immunomodulatory effects.

As shown in TABLE 12 and FIG. 11, the phagocytic activity at M.O.I. of 12.5 was significantly enhanced in the TA-M and TA-H groups as compared to the NC group (p<0.05). In addition, a significant increase of the phagocytic activity of peritoneal macrophages was observed in the TA-L, TA-M, and TA-H groups as compared to the NC group at M.O.I. of 25 and 50 (p<0.05). The result indicated that the phagocytic activity was significantly enhanced by the test article.

TABLE 12

Phagocytic activity of peritoneal macrophages

| | | Phagocytic activity (%) | | |
|---|---|---|---|---|
| | Dose | M.O.I. | | |
| Group | (g/kg/day) | 12.5 | 25 | 50 |
| NC | — | 2.37 ± 1.17 | 6.09 ± 1.59 | 14.31 ± 3.89 |
| TA-L | 0.9 | 4.06 ± 1.42 | 15.15 ± 3.54 | 22.25 ± 3.22 |
| TA-M | 1.8 | 5.82 ± 1.86 | 17.04 ± 4.46 | 26.05 ± 5.68 |
| TA-H | 3.7 | 7.25 ± 2.86 | 19.25 ± 4.21 | 30.68 ± 5.24 |

Data were expressed as mean ± standard deviation (S.D.) of 10 mice, and analyzed using one-way ANOVA followed by Duncan's multiple range test.
NC = negative control; TA-L = test article low dose; TA-M = test article middle dose; TA-H = test article high dose.
Phagocytic activity was indicated as the percentage of macrophages with phagocytized fluorescein-labeled *E. coli*.

2.7 Splenocyte Cytokine Production

Splenocytes (0.5 to 1×10⁶ cells/well) were treated with Con A and LPS. After incubation at 37° C. for 72 hours, cell-free supernatants were collected after centrifugation (300 g, 4° C., 10 minutes), and cytokines including IL-2 (eBioscience, Cat. no. 88-7024), IL-4 (eBioscience, Cat. no. 88-7044), IL-5 (eBioscience, Cat. no. 88-7054), IL-10 (eBioscience, Cat. no. 88-7104), IFN-γ (eBioscience, Cat. no. 88-7314) were measured by ELISA assay kit after 72 hours Con A and LPS stimulation. In addition, TNF-α (eBioscience, Cat. no. 88-7324) was measured after 48 hours Con A and LPS stimulation.

2.7.1 IL-2

Figure 12:
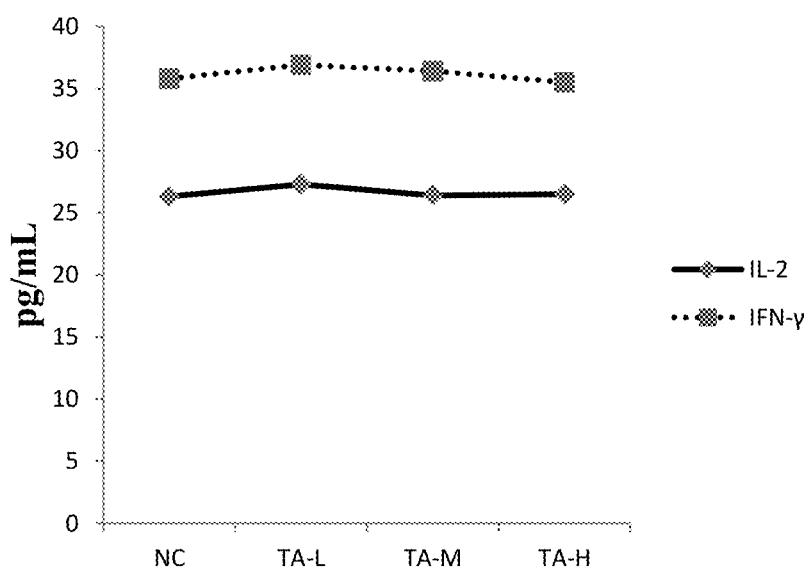
FIG. 12 shows the IL-2 and IFN-γ production without OVA stimulation according to the evaluation study on the non-specific immunomodulatory effects.
Figure 13:
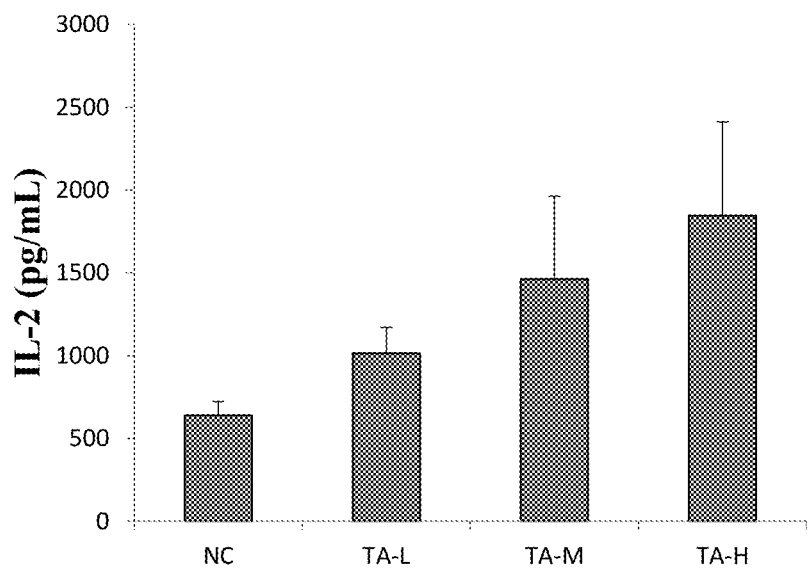
FIG. 13 shows the IL-2 production after Con A stimulation according to the evaluation study on the non-specific immunomodulatory effects.
Figure 14:
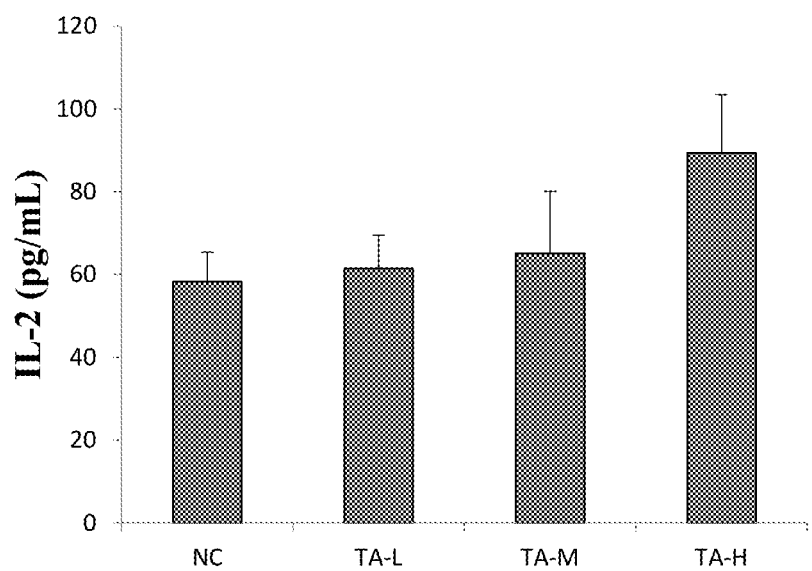
FIG. 14 shows the IL-2 production after LPS stimulation according to the evaluation study on the non-specific immunomodulatory effects.

As shown in TABLE 13 and FIGS. 12 to 14, there were no significant differences in basal levels (without mitogen stimulation) of IL-2 release among all groups (p>0.05). After Con A stimulation, the IL-2 level was significantly increased in the TA-L, TA-M, and TA-H groups as compared to the NC group (p<0.05). In addition, after LPS stimulation, the IL-2 level was significantly increased in the TA-H group as compared to the NC group (p<0.05). The result indicated that the test article promotes IL-2 secretion after mitogen stimulation.

TABLE 13

Cytokines production

| | Unstimulated basal | Mitogen stimulation | |
|---|---|---|---|
| Group | level | Con A(5 µg/mL) | LPS(10 µg/mL) |
| | IL-2(pg/mL) | | |
| NC | 26.3 ± 3.3 | 640.7 ± 83.1 | 58.3 ± 7.1 |
| TA-L | 27.3 ± 5.0 | 1015.9 ± 156.4 | 61.5 ± 8.0 |

TABLE 13-continued

Cytokines production

| Group | Unstimulated basal level | Mitogen stimulation Con A(5 μg/mL) | LPS(10 μg/mL) |
|---|---|---|---|
| TA-M | 26.4 ± 4.3 | 1463.7 ± 499.6 | 65.1 ± 15.0 |
| TA-H | 26.5 ± 4.2 | 1846.3 ± 566.4 | 89.4 ± 14.0 |
| IL-4(pg/mL) | | | |
| NC | 22.8 ± 3.6 | 271.1 ± 87.9 | 88.2 ± 25.5 |
| TA-L | 22.7 ± 2.8 | 247.9 ± 75.9 | 78.6 ± 23.2 |
| TA-M | 23.3 ± 4.0 | 232.3 ± 63.3 | 74.1 ± 18.9 |
| TA-H | 23.1 ± 3.8 | 222.9 ± 57.6 | 67.6 ± 17.8 |
| IL-5(pg/mL) | | | |
| NC | 14.0 ± 1.3 | 206.6 ± 37.7 | 39.6 ± 7.3 |
| TA-L | 14.4 ± 1.9 | 206.8 ± 44.4 | 39.4 ± 8.0 |
| TA-M | 13.9 ± 1.1 | 200.1 ± 33.3 | 33.7 ± 3.9 |
| TA-H | 14.6 ± 1.8 | 198.2 ± 39.6 | 34.7 ± 4.6 |
| IL-10(pg/mL) | | | |
| NC | 133.3 ± 20.2 | 2291.4 ± 188.0 | 356.6 ± 36.1 |
| TA-L | 133.8 ± 20.1 | 2114.3 ± 437.6 | 345.2 ± 85.0 |
| TA-M | 133.8 ± 18.5 | 2100.0 ± 386.9 | 342.9 ± 73.9 |
| TA-H | 135.8 ± 22.7 | 2020.0 ± 283.5 | 337.2 ± 47.0 |
| TNF-α(pg/mL) | | | |
| NC | 8.6 ± 2.5 | 253.5 ± 31.6 | 361.4 ± 63.4 |
| TA-L | 7.8 ± 1.8 | 261.0 ± 50.4 | 392.5 ± 59.0 |
| TA-M | 8.6 ± 2.0 | 267.0 ± 45.2 | 407.0 ± 65.4 |
| TA-H | 8.7 ± 2.1 | 277.7 ± 41.2 | 429.4 ± 56.4 |
| IFN-γ(pg/mL) | | | |
| NC | 35.8 ± 8.1 | 12648.6 ± 2323.4 | 2796.5 ± 1096.7 |
| TA-L | 36.9 ± 10.4 | 20041.4 ± 4689.3 | 2816.5 ± 1177.3 |
| TA-M | 36.4 ± 10.1 | 25768.6 ± 3434.9 | 3177.6 ± 1024.5 |
| TA-H | 35.5 ± 6.5 | 27848.6 ± 4467.0 | 3300.6 ± 842.5 |

Data were expressed as mean ± standard deviation (S.D.) of 10 mice, and analyzed using one-way ANOVA followed by Duncan's multiple range test.
NC = negative control; TA-L = test article low dose; TA-M = test article middle dose; TA-H = test article high dose.

2.7.2 IL-4

Further referring to TABLE 13, there were no significant differences in basal levels (without mitogen stimulation) of IL-4 release among all groups ($p>0.05$). After Con A and LPS stimulation, no significant differences were found among all groups for IL-4 levels ($p>0.05$).

2.7.3 IL-5

Further referring to TABLE 13, there were no significant differences in basal levels (without mitogen stimulation) of IL-5 release among all groups ($p>0.05$). After Con A and LPS stimulation, no significant differences were found among all groups for IL-5 levels ($p>0.05$).

2.7.4 IL-10

Further referring to TABLE 13, there were no significant differences in basal levels (without mitogen stimulation) of IL-10 release among all groups ($p>0.05$). After Con A and LPS stimulation, no significant differences were found among all groups for IL-10 levels ($p>0.05$).

2.7.5 TNF-α

Further referring to TABLE 13, there were no significant differences in basal levels (without mitogen stimulation) of TNF-α release among all groups ($p>0.05$). After Con A and LPS stimulation, TNF-α level was increased in a dose-dependent manner, but no significant differences were found among all groups ($p>0.05$).

2.7.6 IFN-γ

Figure 15:
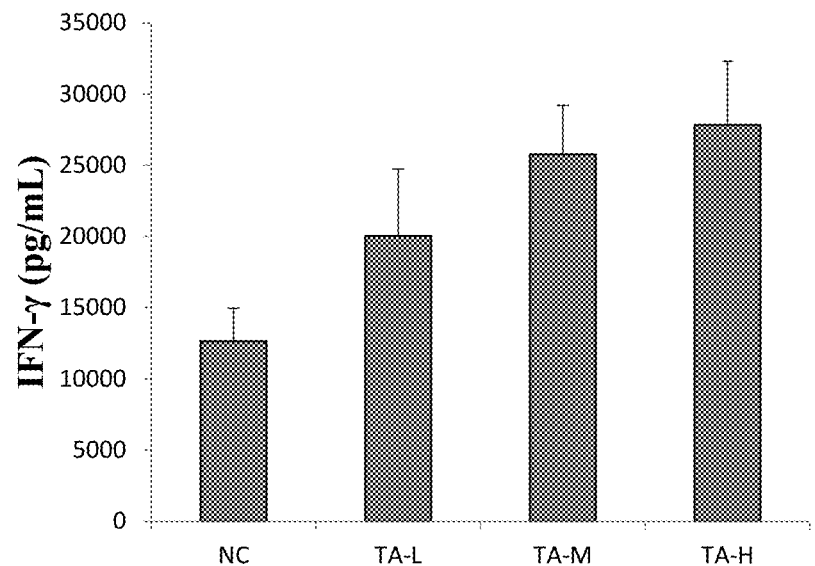
FIG. 15 shows the IFN-γ production after Con A stimulation according to the evaluation study on the non-specific immunomodulatory effects.
Figure 16:
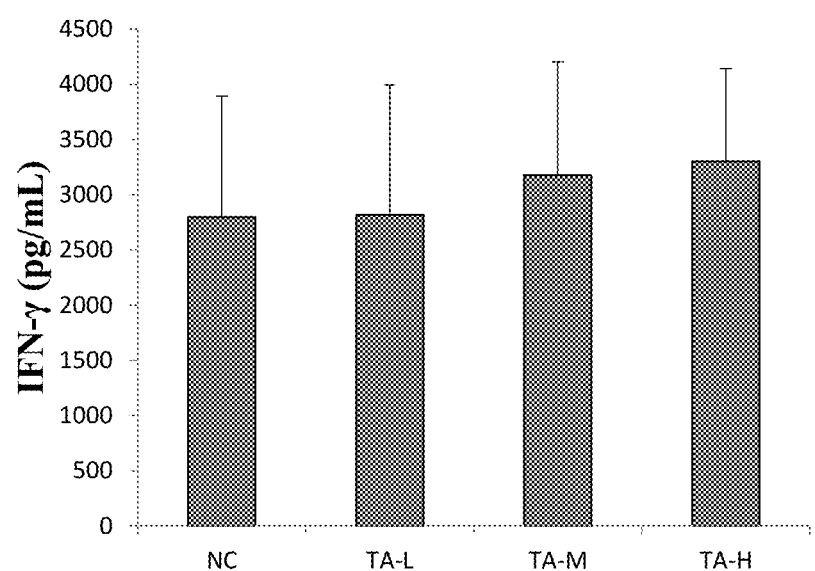
FIG. 16 shows the IFN-γ production after LPS stimulation according to the evaluation study on the non-specific immunomodulatory effects.

As shown in TABLE 13 and FIGS. 12 and 15-16, there were no significant differences in basal levels (without mitogen stimulation) of IFN-γ release among all groups ($p>0.05$). After Con A stimulation, IFN-γ level in the TA-L, TA-M, and TA-H groups was significantly increased as compared to the NC group ($p<0.05$). In addition, IFN-γ level was increased in a dose-dependent manner, but no significant differences were found among all groups ($p>0.05$).

2.8 Serum Levels of Immunoglobulins

After the whole blood samples were centrifugated at 2200 g for 15 minutes, serum samples were collected for further analysis for serum immunoglobulins using mouse IgM, IgE, IgA, and IgG ELISA Quantitation Set (Bethyl Laboratories, Cat. no. E90-101, E90-103, E90-115, and E90-131). As shown in TABLE 14, there were no significant differences among all groups for IgM, IgE, IgA, and IgG levels ($p>0.05$).

TABLE 14

Serum immunoglobulins levels

| Group | Serum antibody (μg/mL) | | | |
|---|---|---|---|---|
|  | IgG | IgM | IgA | IgE |
| NC | 3609.7 ± 207.1 | 312.4 ± 32.9 | 253.2 ± 40.9 | 0.26 ± 0.10 |
| TA-L | 3670.5 ± 206.2 | 315.5 ± 26.3 | 253.8 ± 43.0 | 0.26 ± 0.11 |
| TA-M | 3629.5 ± 194.6 | 317.1 ± 52.1 | 262.4 ± 25.1 | 0.23 ± 0.09 |
| TA-H | 3783.7 ± 276.0 | 314.3 ± 36.5 | 272.4 ± 60.6 | 0.27 ± 0.14 |

Data were expressed as mean ± standard deviation (S.D.) of 10 mice, and analyzed using one-way ANOVA followed by Duncan's multiple range test.
NC = negative control; TA-L = test article low dose; TA-M = test article middle dose; TA-H = test article high dose.

2.9 Cell Surface Marker Analysis

Splenocytes ($5 \times 10^5$ cells/well) were stained with fluorescence-conjugated monoclonal antibodies against T4 cells markers (CD4+/CD3+), T8 cells markers (CD8+/CD3+), T cells markers (CD3+/CD45+), B cells markers (CD19+/CD45+), and NK cells markers (PanNK+/CD45+). Different lymphocyte populations by cell surface markers were quantified by flow cytometry. As shown in TABLE 15, there were no significant differences among all groups.

TABLE 15

Cell surface marker analysis
Immune cell type (%)

| Group | T4 cell (CD4+, CD3+) | T8 cell (CD8+, CD3+) | B cell (CD19+, CD45+) |
|---|---|---|---|
| NC | 30.0 ± 1.7 | 12.5 ± 1.7 | 47.4 ± 1.8 |
| TA-L | 31.7 ± 3.5 | 12.6 ± 1.5 | 48.2 ± 2.7 |
| TA-M | 31.6 ± 1.8 | 12.1 ± 1.4 | 47.2 ± 3.3 |
| TA-H | 31.3 ± 2.8 | 12.9 ± 1.8 | 48.8 ± 2.7 |

Cell surface marker analysis
Immune cell type (%)

| Group | T cell (CD3+, CD45+) | NK cell (PanNK+, CD45+) |
|---|---|---|
| NC | 42.1 ± 3.5 | 7.5 ± 0.9 |
| TA-L | 43.9 ± 4.7 | 7.2 ± 0.8 |
| TA-M | 44.5 ± 3.3 | 7.3 ± 1.1 |
| TA-H | 42.9 ± 4.5 | 7.7 ± 0.9 |

Data were expressed as mean ± standard deviation (S.D.) of 10 mice, and analyzed using one-way ANOVA followed by Duncan's multiple range test.
NC = negative control; TA-L = test article low dose; TA-M = test article middle dose; TA-H = test article high dose.

With the aforementioned results, as shown in TABLE 16, the test article could promote the proliferative response of splenic lymphocytes, the phagocytic activity of peritoneal macrophages, and the cytolytic activity of NK cells. In addition, after mitogen stimulation, the test article could promote the production of IL-2 and IFN-γ. Whereby, the *Ganoderma lucidum* polysaccharides composite composition has the potential immunomodulatory effects on non-specific immunity.

TABLE 16

Summary of the immunomodulatory effects of the
*Ganoderma lucidum* polysaccharides composite
composition on the non-specific immunity

| Testing parameters | | | TA-L | TA-M | TA-H |
|---|---|---|---|---|---|
| Splenocyte proliferation | | Con A | p < 0.05↑ | p < 0.05↑ | p < 0.05↑ |
| | | LPS | — | — | p < 0.05↑ |
| Cytokines production | IL-2 | Con A | p < 0.05↑ | p < 0.05↑ | p < 0.05↑ |
| | | LPS | — | — | p < 0.05↑ |
| | IL-4 | Con A | — | — | — |
| | | LPS | — | — | — |
| | IL-5 | Con A | — | — | — |
| | | LPS | — | — | — |
| | IL-10 | Con A | — | — | — |
| | | LPS | — | — | — |
| | TNF-α | Con A | — | — | — |
| | | LPS | — | — | — |
| | IFN-γ | Con A | p < 0.05↑ | p < 0.05↑ | p < 0.05↑ |
| | | LPS | — | — | — |
| Spleen lymphocyte populations | T4 cell | | — | — | — |
| | T8 cell | | — | — | — |
| | T cell | | — | — | — |
| | B cell | | — | — | — |
| | NK cell | | — | — | — |
| Serum antibody | IgG | | — | — | — |
| | IgM | | — | — | — |
| | IgA | | — | — | — |
| | IgE | | — | — | — |
| NK cell activity | E/T ratio = 10:1 | | p < 0.05↑ | p < 0.05↑ | p < 0.05↑ |
| | E/T ratio = 25:1 | | p < 0.05↑ | p < 0.05↑ | p < 0.05↑ |
| Phagocytic activity | M.O.I. = 12.5 | | — | p < 0.05↑ | p < 0.05↑ |
| | M.O.I. = 25 | | p < 0.05↑ | p < 0.05↑ | p < 0.05↑ |
| | M.O.I. = 50 | | p < 0.05↑ | p < 0.05↑ | p < 0.05↑ |

—: no significant difference as compared to the NC group
p < 0.05↑: significantly increased as compared to the NC group
p < 0.05↑: significantly decreased as compared to the NC group With the aforementioned results, the *Ganoderma lucidum* polysaccharides composite composition has the potential immunomodulatory effects on the specific and non-specific immunity.

It must be pointed out that the embodiments described above are only some embodiments of the present invention. All equivalent structures which employ the concepts disclosed in this specification and the appended claims should fall within the scope of the present invention.

What is claimed is:

1. A composition for promoting an immunomodulatory effect in a subject comprising an effective amount of an extract mixture, wherein said mixture comprises: 1 to 5 wt. % β-glucan extract, 1 to 5 wt. % *Ganoderma lucidum* mycelium extract, 1 to 5 wt. % *Trametes versicolor* mycelium extract, 1 to 5 wt. % *Tremella fuciformis* Berk extract, 1 to 5 wt. % *Auricularia auricula-judae* extract, 0.5 to 5 wt. % *Hericium erinaceus* extract, 0.2 to 3 wt. % *Ganoderma lucidum* fruiting body extract, and water;
   wherein the β-glucan extract is extracted from a fermented culture of *Aureobasidium pullulans*;
   wherein polysaccharides concentration of the B-glucan extract is 10 g/L, polysaccharides concentration of the *Ganoderma lucidum* mycelium extract is 5 g/L, polysaccharides concentration of the *Trametes versicolor* mycelium extract is 5 g/L, polysaccharides concentration of the *Tremella fuciformis* Berk extract is 10 g/L, polysaccharides concentration of the *Auricularia auricula-judae* extract is 10 g/L, polysaccharides concentration of the *Hericium erinaceus* extract is 5 g/L, and polysaccharides concentration of the *Ganoderma lucidum* fruiting body extract is 5 g/L; and
   wherein the fermented culture of *Aureobasidium pullulans* for extracting the β-glucan extract is obtained by a method comprising: culturing a microorganism of *Aureobasidium pullulans* in a culture medium, wherein the culture medium has a pH of 5.0 to 6.5 and comprises, based on a total culture medium, 0.5 to 5.0 wt. % carbon source, 0.1 to 1.5 wt. % nitrogen source and trace elements; and then incubating each of the culture media in air at 20 to 30° C. for 2 to 7 days with stirring for producing the fermented culture.

2. The composition of claim 1, further comprising a flavor modulator, wherein the flavor modulator comprises citric acid.

3. The composition of claim 1, further comprising a sweetener, wherein the sweetener comprises acesulfame potassium.

4. The composition of claim 1, further comprising a juice concentrate, wherein the juice concentrate comprises orange juice concentrate.

5. The composition of claim 1, wherein the composition is provided in a powder form, a beverage form, or an encapsulated form.

6. The composition of claim 1, wherein the effective amount of the extract mixture comprises: 3 wt. % β-glucan extract, 3 wt. % *Ganoderma lucidum* mycelium extract, 2.5 wt. % *Trametes versicolor* mycelium extract, 3 wt. % *Tremella fuciformis* Berk extract, 2.5 wt. % *Auricularia auricula-judae* extract, 0.5 wt. % *Hericium erinaceus* extract, and 0.2 wt. % *Ganoderma lucidum* fruiting body extract.

7. A method of promoting an immunomodulatory effect comprising administering an effective amount of the composition according to claim 1 to a subject in need thereof.

* * * * *